US011332458B2

(12) United States Patent
Nakagawa et al.

(10) Patent No.: US 11,332,458 B2
(45) Date of Patent: May 17, 2022

(54) METHOD FOR PREPARING N-ALKOXYCARBONYLPIPERIDINE DERIVATIVE, AND INTERMEDIATE THEREFOR

(71) Applicant: YUKI GOSEI KOGYO CO., LTD., Tokyo (JP)

(72) Inventors: Kiyono Nakagawa, Tokyo (JP); Yoshihiro Ito, Tokyo (JP); Yumiko Tanaka, Tokyo (JP)

(73) Assignee: YUKI GOSEI KOGYO CO., LTD., Tokyo (JP)

( * ) Notice: Subject to any disclaimer, the term of this patent is extended or adjusted under 35 U.S.C. 154(b) by 74 days.

(21) Appl. No.: 16/962,394

(22) PCT Filed: Jan. 18, 2019

(86) PCT No.: PCT/JP2019/001426
§ 371 (c)(1),
(2) Date: Dec. 16, 2020

(87) PCT Pub. No.: WO2019/142900
PCT Pub. Date: Jul. 25, 2019

(65) Prior Publication Data
US 2021/0122729 A1 Apr. 29, 2021

(30) Foreign Application Priority Data

Jan. 19, 2018 (JP) ............................. JP2018-007427

(51) Int. Cl.
*C07D 401/06* (2006.01)
(52) U.S. Cl.
CPC .................. *C07D 401/06* (2013.01)
(58) Field of Classification Search
CPC .... C07D 211/46; C07D 211/70; C07D 401/06
See application file for complete search history.

(56) References Cited

U.S. PATENT DOCUMENTS

| 6,900,326 B2* | 5/2005 | Nakagawa | ........... | C07D 211/46 |
| | | | | 546/188 |
| 2004/0063953 A1 | 4/2004 | Nakagawa | | |
| 2004/0122232 A1 | 6/2004 | Chen et al. | | |
| 2006/0074241 A1 | 4/2006 | Chen et al. | | |

FOREIGN PATENT DOCUMENTS

| JP | 2004131486 A | 4/2004 |
| JP | 2006104130 A | 4/2006 |
| JP | 2006511481 A | 4/2006 |
| WO | 98/57962 A1 | 12/1998 |
| WO | 98/57968 A1 | 12/1998 |
| WO | 2004/031153 A2 | 4/2004 |

OTHER PUBLICATIONS

International Search Report (and English translation) and Written Opinion of the International Searching Authority for PCT/JP2019/001426 dated Feb. 19, 2019.

* cited by examiner

*Primary Examiner* — Deepak R Rao
(74) *Attorney, Agent, or Firm* — Heslin Rothenberg Farley & Mesiti P.C.

(57) ABSTRACT

The object of the present invention is to provide a simple method for preparing an N-alkoxycarbonyl piperidine derivative.

The object can be solved by a method for preparing a hydroxypiperidine derivative, comprising a step of:

(A) reacting a piperidylidene acetic acid derivative represented by the formula (1):

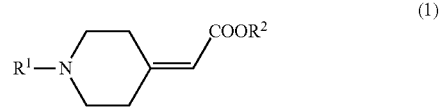

(1)

wherein $R^1$ is an aralkyl group which may have a substituent group, and $R^2$ is an alkyl group, with 4-hydroxypiperidine in the presence of base, to obtain a hydroxypiperidine derivative represented by the formula (2) or the formula (3):

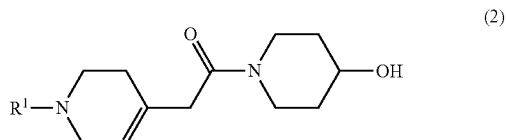

(2)

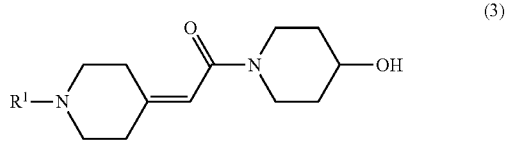

(3)

wherein $R^1$ is an aralkyl group which may have a substituent group.

7 Claims, No Drawings

METHOD FOR PREPARING N-ALKOXYCARBONYLPIPERIDINE DERIVATIVE, AND INTERMEDIATE THEREFOR

TECHNICAL FIELD

The present invention relates to a method for preparing a N-alkoxycarbonyl piperidine derivative and an intermediate thereof.

BACKGROUND ART

It is disclosed that 1-(1-tert-butoxycarbonyl-4-piperidylacetyl)-4-mesyloxypiperidine is useful, for example, as an intermediate for synthesizing farnesyl protein transferase inhibitor (Patent literature 1).

Patent literature 2 discloses that the method for preparing 1-(1-tert-butoxycarbonyl-4-piperidylacetyl)-4-mesyloxypiperidine using an N-aralkylpiperidine derivative which a novel compound. Specifically, the following methods are disclosed. N-aralkylpiperidine derivative is reacted with mesyl halide in the presence of base, and the obtained mesyl compound is reacted with a dicarbonate in the presence of hydrogen and a catalyst containing palladium, to thereby prepare N-alkoxycarbonyl piperidine derivative (1-(1-tert-butoxycarbonyl-4-piperidylacetyl)-4-mesyloxypiperidine). Further, An N-aralkylpiperidine derivative is reacted with a dicarbonate, and the obtained alkoxycarbonyl derivative is reacted mesyl halide, to thereby prepare N-alkoxycarbonyl piperidine derivative (1-(1-tert-butoxycarbonyl-4-piperidylacetyl)-4-mesyloxypiperidine (Patent literature 2).

CITATION LIST

Patent Literature

[Patent literature 1] Japanese Translation Publication (Kohyo) No. 2006-511481
[Patent literature 2] Japanese Unexamined Patent Publication (Kokai) No. 2004-131486

SUMMARY OF INVENTION

Technical Problem

The object of the present invention is to provide a simple method for preparing an N-alkoxycarbonyl piperidine derivative. In addition, the object of the present invention is to provide an N-alkoxycarbonyl piperidine derivative containing few impurities.

Solution to Problem

The present inventors have conducted intensive studies for the simple method for preparing an N-alkoxycarbonyl piperidine derivative, and as a result, surprisingly found a novel hydroxypiperidine derivative obtained by reacting piperidylidene acetic acid derivative with 4-hydroxypiperidine, and found that an N-alkoxycarbonyl piperidine derivative can be easily prepared using the above compound.

The present invention is based on the above findings.
Accordingly, the present invention relates to
[1] a method for preparing a hydroxypiperidine derivative, comprising a step of:
(A) reacting a piperidylidene acetic acid derivative represented by the formula (1):

[Chem. 1]

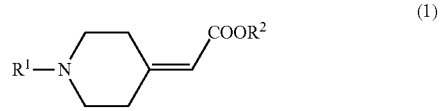

wherein $R^1$ is an aralkyl group which may have a substituent group, and $R^2$ is an alkyl group, with 4-hydroxypiperidine in the presence of base, to obtain a hydroxypiperidine derivative represented by the formula (2) or the formula (3):

[Chem. 2]

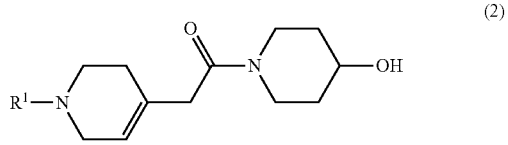

[Chem. 3]

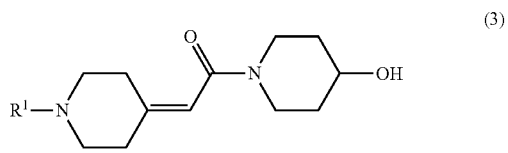

wherein $R^1$ is an aralkyl group which may have a substituent group,
[2] a method for preparing an N-alkoxycarbonyl piperidine derivative, comprising the steps of:
(A) of the item [1],
(B) reacting the hydroxypiperidine derivative obtained in the step (A) with a dicarbonate represented by the formula (4):

[Chem. 4]

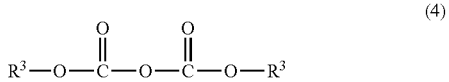

wherein $R^3$ is alkyl group, in the presence of hydrogen and a catalyst containing palladium,
to obtain an alkoxycarbonyl derivative represented by the formula (5):

[Chem. 5]

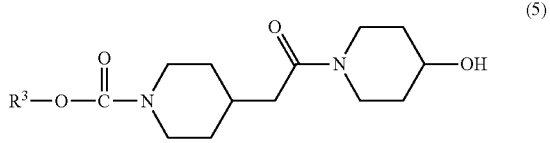

wherein R³ is an alkyl group, and
(C) reacting the alkoxycarbonyl derivative with mesyl halide in the presence of base, to obtain an N-alkoxycarbonyl piperidine derivative represented by the formula (6):

[Chem. 6]

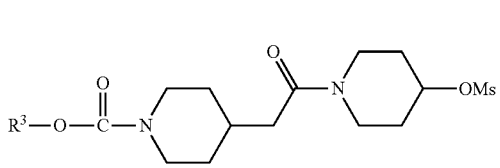

(6)

wherein R³ is an alkyl group, and Ms is a mesyl group,
[3] a method for preparing an N-alkoxycarbonyl piperidine derivative, comprising the steps of:
(A) of the item [1],
(D) reacting the hydroxypiperidine derivative obtained in the step (A) with mesyl halide in the presence of base, to obtain a mesyloxypiperidine derivative represented by the formula (7) or the formula (8):

[Chem. 7]

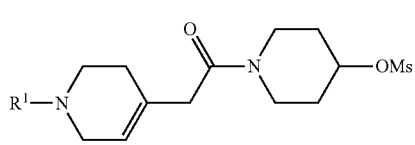

(7)

[Chem. 8]

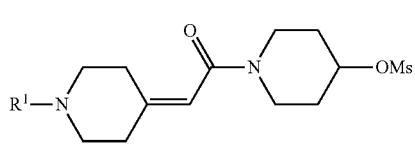

(8)

wherein R¹ is an aralkyl group which may have a substituent group, and
(E) reacting the mesyloxypiperidine derivative with a dicarbonate represented by the formula (4):

[Chem. 9]

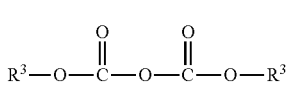

(4)

wherein R³ is alkyl group, in the presence of hydrogen and a catalyst containing palladium, to obtain an N-alkoxycarbonyl piperidine derivative represented by the formula (6):

[Chem. 10]

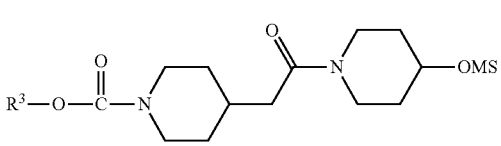

(6)

wherein R³ is an alkyl group, and Ms is a mesyl group,
[4] 1-(1-benzyl-4-piperidylideneacetyl)-4-hydroxypiperidine represented by the formula (9):

[Chem. 11]

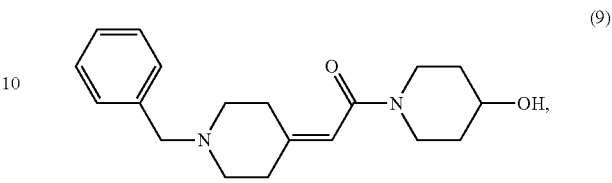

(9)

[5] 1-(1-benzyl-1,2,3,6-tetrahydropyridine-4-ylacetyl)-4-hydroxypiperidine represented by the formula (10):

[Chem. 12]

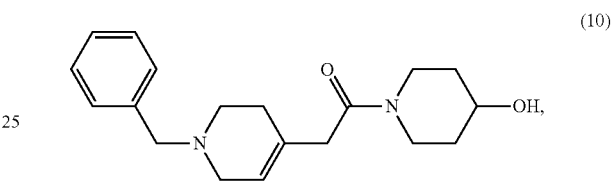

(10)

[6] 1-(1-benzyl-4-piperidylideneacetyl)-4-mesyloxypiperidine represented by the formula (11):

[Chem. 13]

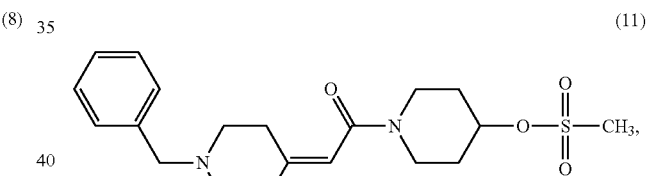

(11)

and
[7] 1-(1-benzyl-1,2,3,6-tetrahydropyridine-4-ylacetyl)-4-mesyloxypiperidine represented by the formula (12):

[Chem. 14]

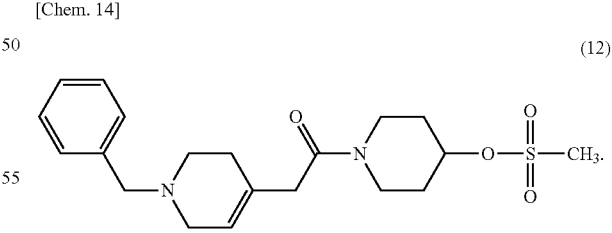

(12)

Advantageous Effects of Invention

According to the method for preparing an N-alkoxycarbonyl piperidine derivative of the present invention, the N-alkoxycarbonyl piperidine derivative can be prepared in a small number of steps compared to conventional preparation methods. Further, the N-alkoxycarbonyl piperidine derivative obtained by the preparation method of the present invention has a much smaller amount of by-products, compared to an N-alkoxycarbonyl piperidine derivative prepared by the preparation method disclosed in Patent literature 2.

DESCRIPTION OF EMBODIMENTS

[1] Method for Preparing N-Alkoxycarbonyl Piperidine Derivative

A first embodiment of the method for preparing an N-alkoxycarbonyl piperidine derivative of the present invention comprises the steps of:
(A) reacting a piperidylidene acetic acid derivative represented by the formula (1) with 4-hydroxypiperidine in the presence of base, to obtain a hydroxypiperidine derivative represented by the formula (2) or the formula (3) (hereinafter sometimes referred to as the step (A)),
(B) reacting the hydroxypiperidine derivative obtained in the step (A) with a dicarbonate represented by the formula (4) in the presence of hydrogen and a catalyst containing palladium, to obtain an alkoxycarbonyl derivative represented by the formula (5) (hereinafter sometimes referred to as the step (B)), and
(C) reacting the alkoxycarbonyl derivative with mesyl halide in the presence of base, to obtain an N-alkoxycarbonyl piperidine derivative represented by the formula (6) (hereinafter sometimes referred to as the step (C)).

A second embodiment of the method for preparing an N-alkoxycarbonyl piperidine derivative of the present invention comprises the steps of:
(A) reacting a piperidylidene acetic acid derivative represented by the formula (1) with 4-hydroxypiperidine in the presence of base, to obtain a hydroxypiperidine derivative represented by the formula (2) or the formula (3),
(D) reacting the hydroxypiperidine derivative obtained in the step (A) with mesyl halide in the presence of base, to obtain a mesyloxypiperidine derivative represented by the formula (7) or the formula (8) (hereinafter sometimes referred to as the step (D)), and
(E) reacting the mesyloxypiperidine derivative with a dicarbonate represented by the formula (4) in the presence of hydrogen and a catalyst containing palladium, to obtain an N-alkoxycarbonyl piperidine derivative represented by the formula (6) (hereinafter sometimes referred to as the step (E)).

The term "aralkyl group which may have a substituent group" as used herein comprises an aralkyl group and an aralkyl group having substituent group. In the aralkyl group, one of hydrogen atoms of the alkyl group is replaced by an aryl group. The number of carbon atoms in the aralkyl group is not limited, but is preferably 7 to 16, more preferably 7 to 10.

The substituent group of the aralkyl group having a substituent group is not limited, but includes halogen atom, an alkyl group, an alkoxy group, an acyl group, an alkoxycarbonyl group, or a nitro group. The number of carbon atoms in the aralkyl group having a substituent group is not limited, but is preferably 7 to 16, more preferably 7 to 10. In this case, the number of carbon atoms in the substituent group is not included therein.

Specifically, the aralkyl group which may have a substituent group includes benzyl group, phenethyl group, α-methylbenzyl group, p-methylbenzyl group, p-nitrobenzyl group, or p-methoxybenzyl group.

The alkyl group is not particularly limited, but is preferably an alkyl group having 1 to 6 carbon atoms, more preferably an alkyl group having 2 to 5 carbon atoms, most preferably an alkyl group having 2 to 4 is most preferable alkyl group. Specifically, the alkyl group includes methyl group, ethyl group, n-propyl group, isopropyl group, n-butyl group, 2-butyl group, isobutyl group, tert-butyl group, n-pentyl group, tert-pentyl group, cyclopentyl group, hexyl group, or cyclohexyl group.

The piperidylidene acetic acid derivative represented by the formula (1), which is a starting material for the preparation method of the N-alkoxycarbonyl piperidine derivative of the present invention, can be prepared by the method described in Patent literature 2, although not limited thereto.

Specifically, a piperidone derivative represented by the formula (13):

[Chem. 15]

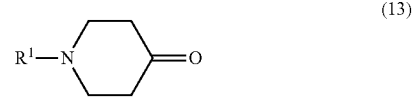

(13)

wherein $R^1$ is an aralkyl group which may have a substituent group, is reacted with a phosphorus reagent represented by the formula (14):

[Chem. 16]

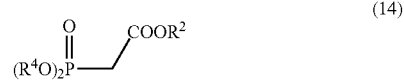

(14)

wherein $R^2$ is an alkyl group, and $R^4$ is an alkyl group or an aryl group, in the presence of base, to obtain a piperidylidene acetic acid derivative represented by the above formula (1).

The alkyl group is not limited, but preferably an alkyl group having 1 to 6 carbon atoms, and there may be mentioned, for example, methyl group, ethyl group, propyl group, isopropyl group, n-butyl group, isobutyl group, tert-butyl group, n-pentyl group, tert-pentyl group, hexyl group, or the like.

The aryl group is not limited, but preferably an aryl group having 6 to 10 carbon atoms, and there may be mentioned phenyl group or naphthyl group.

As the phosphorus reagent, there may be mentioned methyl dimethylphosphonoacetate, ethyl diethylphosphonoacetate, ethyl diphenylphosphonoacetate. It is preferably ethyl diethylphosphonoacetate. The phosphorus reagent may be used in a stoichiometric amount to the piperidone derivative. That is, an equimolar amount thereto is sufficient, preferably 1 to 1.5 times by mol.

As the base, there may be mentioned sodium methoxide, potassium methoxide, sodium ethoxide, potassium ethoxide, sodium tert-butoxide, potassium tert-butoxide, sodium hydride, potassium hydride, sodium carbonate, potassium carbonate, sodium hydroxide, potassium hydroxide or the like, and alkali metal alkoxides such as sodium methoxide and sodium ethoxide are preferable. The base may be used in a stoichiometric amount to the piperidone derivative. That is, an equimolar amount thereto is sufficient, preferably 1 to 1.2 times by mol.

Generally, the reaction may be carried out in a solvent. The solvent used is not particularly limited as long as it does not inhibit the reaction, and there may be mentioned, for example, alcohols such as methanol, ethanol, 2-propanol, n-butanol or tert-butanol; ethers such as diethyl ether, tetrahydrofuran, or dioxane; hydrocarbons such as benzene, toluene, or xylene; or nitriles such as acetonitrile. These solvents may be used alone or in combination.

The reaction temperature varies depending on the raw materials (including solvent), but it is usually −10 to 30° C. The reaction time varies depending on the raw materials and the reaction temperature, but the reaction is usually completed within 1 to 5 hours.

In the method for preparing a N-alkoxycarbonyl piperidine derivative of the present invention, the piperidylidene acetic acid derivative represented by the formula (1) is reacted in the order of step (A), step (B), and step (C), to thereby obtain the N-alkoxycarbonyl piperidine derivative. The piperidylidene acetic acid derivative is reacted in the order of step (A), step (D), and step (E), to thereby obtain the N-alkoxycarbonyl piperidine derivative.

<<Step (A)>>

In the step (A), the piperidylidene acetic acid derivative represented by the formula (1) is reacted with 4-hydroxypiperidine in the presence of base, to obtain the hydroxypiperidine derivative represented by the formula (2) or the formula (3)

The piperidylidene acetic acid derivative is not limited, but includes, for example, 1-benzyl-4-piperidylidene acetic acid ethyl ester.

4-hydroxypiperidine may be used in a stoichiometric amount to the piperidylidene acetic acid derivative. That is, an equimolar amount thereto is sufficient, preferably 1 to 1.5 times by mol.

As the base used in the step (A), there may be mentioned sodium methoxide, potassium methoxide, sodium ethoxide, potassium ethoxide, sodium tert-butoxide, potassium tert-butoxide, sodium hydride, potassium hydride, sodium carbonate, potassium carbonate, sodium hydroxide, potassium hydroxide or the like, and alkali metal alkoxides such as sodium methoxide and sodium ethoxide are preferable. The base may be used sufficiently in an about equimolar amount to the piperidylidene acetic acid derivative, and it is preferably 0.5 to 1.5 times by mol.

Generally, the reaction may be carried out in a solvent. The solvent used is not particularly limited as long as it does not inhibit the reaction, and there may be mentioned, for example, alcohols such as methanol, ethanol, 2-propanol, n-butanol or tert-butanol; ethers such as diethyl ether, tetrahydrofuran, or dioxane; hydrocarbons such as benzene, toluene, or xylene. These solvents may be used alone or in combination.

The reaction temperature varies depending on the raw materials (including solvent), but it is usually 50 to 120° C. The reaction time varies depending on the raw materials and the reaction temperature, but the reaction is usually completed within 1 to 10 hours.

The hydroxypiperidine derivative represented by the formula (2) includes, for example, 1-(1-benzyl-1,2,3,6-tetrahydropyridine-4-ylacetyl)-4-hydroxypiperidine. The hydroxypiperidine derivative represented by the formula (3) includes, for example, 1-(1-benzyl-4-piperidylideneacetyl)-4-hydroxypiperidine.

<<Step (B)>>

In the step (B), the hydroxypiperidine derivative is reacted with a dicarbonate represented by the formula (4) in the presence of hydrogen and a catalyst containing palladium, to obtain an alkoxycarbonyl derivative represented by the formula (5).

As the dicarbonate, there may be mentioned dimethyl dicarbonate, diethyl dicarbonate, dipropyl dicarbonate, diisopropyl dicarbonate, dibutyl dicarbonate, diisobutyl dicarbonate, di-tert-butyl dicarbonate, di-tert-amyl decarbonate or the like. Dicarbonate may be used in a stoichiometric amount to the hydroxypiperidine derivative. That is, an equimolar amount thereto is sufficient, preferably 1 to 1.5 times by mol.

The catalyst is not particularly limited as long as it contains palladium. For example, there may be mentioned a palladium-carbon, a palladium-alumina, a palladium-silica, a palladium-barium sulfate, or the like. A palladium-carbon is preferable. The catalyst may be used sufficiently in a small amount (in palladium equivalent) to the N-aralkylpiperidine derivative, and is usually 0.05 to 2% by mass. The hydrogen pressure is not particularly limited, but is preferably in the range of ordinary pressure to 1 MPa.

Generally, the reaction may be carried out in a solvent. The solvent used is not particularly limited as long as it does not inhibit the reaction, and there may be mentioned, for example, alcohols such as methanol, ethanol, 2-propanol, n-butanol or tert-butanol; ethers such as diethyl ether, tetrahydrofuran, or dioxane; hydrocarbons such as benzene, toluene, or xylene. These solvents may be used alone or in combination.

The reaction temperature varies depending on the raw materials (including solvent), but it is usually 30 to 80° C. The reaction time varies depending on the raw materials and the reaction temperature, but the reaction is usually completed within 1 to 8 hours.

The obtained alkoxycarbonyl derivatives are not limited, but include, for example, 1-(1-tert-butoxycarbonyl-4-piperidylacetyl)-4-hydroxypiperidine.

<<Step (C)>>

In the step (C), the alkoxycarbonyl derivative is reacted with mesyl halide in the presence of base, to obtain the N-alkoxycarbonyl piperidine derivative represented by the formula (6).

Mesyl halide includes mesyl chloride or the like, and the base includes pyridine, dimethylamine, diethylamine, triethylamine, tributylamine, triethanolamine, or the like.

The base may be used in a stoichiometric amount to mesyl halide. That is, an equimolar amount thereto is sufficient, preferably 1 to 1.5 times by mol.

Mesyl halide may be used in a stoichiometric amount to alkoxycarbonyl derivative. That is, an equimolar amount thereto is sufficient, preferably 1 to 1.5 times by mol.

Generally, the reaction may be carried out in a solvent. The solvent used is not particularly limited as long as it does not inhibit the reaction, and there may be mentioned, for example, esters such as ethyl acetate, ethyl propionate; ethers such as diethyl ether, tetrahydrofuran, or dioxane; hydrocarbons such as benzene, toluene, or xylene; halogenated hydrocarbons such as dichloromethane, dichloroethane, or chloroform; or nitriles such as acetonitrile. These solvents may be used alone or in combination.

The reaction temperature varies depending on the raw materials (including solvent), but it is usually −10 to 20° C. The reaction time varies depending on the raw materials and the reaction temperature, but the reaction is usually completed within 1 to 5 hours.

The N-alkoxycarbonyl piperidine derivative is not limited, but includes, for example, 1-(1-tert-butoxycarbonyl-4-piperidylacetyl)-4-mesyloxypiperidine.

<<Step (D)>>

In the step (D), hydroxypiperidine derivative is reacted with mesyl halide in the presence of base, to obtain a mesyloxypiperidine derivative represented by the formula (7) or the formula (8).

Mesyl halide includes mesyl chloride or the like, and the base includes pyridine, dimethylamine, diethylamine, triethylamine, tributylamine, triethanolamine, or the like.

The base may be used in a stoichiometric amount to mesyl halide. That is, an equimolar amount thereto is sufficient, preferably 1 to 1.5 times by mol.

Mesyl halide may be used in a stoichiometric amount to the hydroxypiperidine derivative. That is, an equimolar amount thereto is sufficient, preferably 1 to 1.5 times by mol.

Generally, the reaction may be carried out in a solvent. The solvent used is not particularly limited as long as it does not inhibit the reaction, and there may be mentioned, for example, esters such as ethyl acetate, ethyl propionate; ethers such as diethyl ether, tetrahydrofuran, or dioxane; hydrocarbons such as benzene, toluene, or xylene; halogenated hydrocarbons such as dichloromethane, dichloroethane, or chloroform; or nitriles such as acetonitrile. These solvents may be used alone or in combination.

The reaction temperature varies depending on the raw materials (including solvent), but it is usually −10 to 20° C. The reaction time varies depending on the raw materials and the reaction temperature, but the reaction is usually completed within 1 to 5 hours.

The mesyloxypiperidine derivative represented by the formula (7) is not limited, but includes, for example, 1,2,3,6-tetrahydropyridine-4-ylacetyl)-4-mesyloxypiperidine.

The mesyloxypiperidine derivative represented by the formula (8) is not limited, but includes, for example, 1-(1-benzyl-4-piperidylideneacetyl)-4-mesyloxypiperidine.

<<Step (E)>>

In the step (E), the mesyloxypiperidine derivative is reacted with a dicarbonate represented by the formula (4) in the presence of hydrogen and a catalyst containing palladium, to obtain an N-alkoxycarbonyl piperidine derivative represented by the formula (6).

As the dicarbonate, there may be mentioned dimethyl dicarbonate, diethyl dicarbonate, dipropyl dicarbonate, diisopropyl dicarbonate, dibutyl dicarbonate, diisobutyl dicarbonate, di-tert-butyl dicarbonate, di-tert-amyl decarbonate or the like. The dicarbonate may be used in a stoichiometric amount to the mesyloxypiperidine derivative. That is, an equimolar amount thereto is sufficient, preferably 1 to 1.5 times by mol.

The catalyst is not particularly limited as long as it contains palladium. For example, there may be mentioned a palladium-carbon, a palladium-alumina, a palladium-silica, a palladium-barium sulfate, or the like. A palladium-carbon is preferable. The catalyst may be used sufficiently in a small amount (in palladium equivalent) to the mesyl compound, and is usually 0.05 to 2% by mass. The hydrogen pressure is not particularly limited, but is preferably in the range of ordinary pressure to 1 MPa Generally, the reaction may be carried out in a solvent. The solvent used is not particularly limited as long as it does not inhibit the reaction, and there may be mentioned, for example, alcohols such as methanol, ethanol, 2-propanol, n-butanol or tert-butanol; esters such as ethyl acetate, ethyl propionate; ethers such as diethyl ether, tetrahydrofuran, or dioxane; hydrocarbons such as benzene, toluene, or xylene. These solvents may be used alone or in combination.

The reaction temperature varies depending on the raw materials (including solvent), but it is usually 30 to 80° C. The reaction time varies depending on the raw materials and the reaction temperature, but the reaction is usually completed within 1 to 8 hours.

The N-alkoxycarbonyl piperidine derivative is not limited, but includes, 1-(1-tert-butoxycarbonyl-4-piperidylacetyl)-4-mesyloxypiperidine.

(Method for Preparing Hydroxypiperidine Derivative)

Hydroxypiperidine derivatives may be prepared by the step (A) of the method for preparing an N-alkoxycarbonyl piperidine derivative of the present invention. That is, the method for preparing hydroxypiperidine derivative comprises a step of reacting a piperidylidene acetic acid derivative represented by the formula (1) with 4-hydroxypiperidine in the presence of base, to obtain a hydroxypiperidine derivative represented by the formula (2) or the formula (3).

The hydroxypiperidine derivative obtained by the preparation method of the present invention may be availably used as a raw material of the N-alkoxycarbonyl piperidine derivatives.

[2] 1-(1-benzyl-4-piperidylideneacetyl)-4-hydroxypiperidine 1-(1-benzyl-4-piperidylideneacetyl)-4-hydroxypiperidine of the present invention is a compound represented by the formula (9):

[Chem. 17]

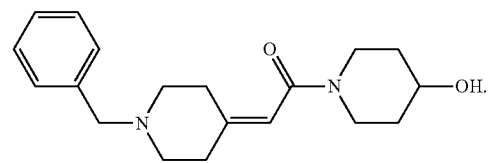

(9)

1-(1-benzyl-4-piperidylideneacetyl)-4-hydroxypiperidine may be prepared by using 1-benzyl-4-piperidylidene acetic acid ethyl ester as the piperidylidene acetic acid derivative in the step (A). 1-(1-benzyl-4-piperidylideneacetyl)-4-hydroxypiperidine is useful for an intermediate of a medicine.

[3] 1-(1-benzyl-1,2,3,6-tetrahydropyridine-4-ylacetyl)-4-hydroxypiperidine 1-(1-benzyl-1,2,3,6-tetrahydropyridine-4-ylacetyl)-4-hydroxypiperidine of the present invention is a compound represented by the formula (10):

[Chem. 18]

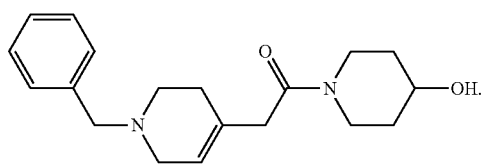

(10)

1-(1-benzyl-1,2,3,6-tetrahydropyridine-4-ylacetyl)-4-hydroxypiperidine may be prepared by using 1-benzyl-4-piperidylidene acetic acid ethyl ester as the piperidylidene acetic acid derivative in the step (A). 1-(1-benzyl-1,2,3,6-tetrahydropyridine-4-ylacetyl)-4-hydroxypiperidine is useful for an intermediate of a medicine.

[4] 1-(1-benzyl-4-piperidylideneacetyl)-4-mesyloxypiperidine 1-(1-benzyl-4-piperidylideneacetyl)-4-mesyloxypiperidine of the present invention is a compound represented by the formula (11):

[Chem. 19]

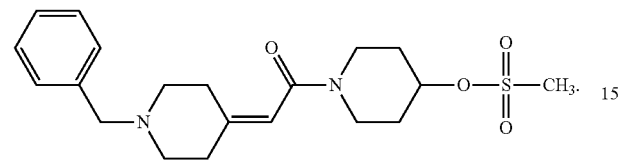

(11)

1-(1-benzyl-4-piperidylideneacetyl)-4-mesyloxypiperidine may be prepared by using 1-(1-benzyl-4-piperidylideneacetyl)-4-hydroxypiperidine as the hydroxypiperidine derivative in the step (D). 1-(1-benzyl-4-piperidylideneacetyl)-4-mesyloxypiperidine is useful for an intermediate of a medicine.

[5] 1-(1-benzyl-1,2,3,6-tetrahydropyridine-4-ylacetyl)-4-mesyloxypiperidine 1-(1-benzyl-1,2,3,6-tetrahydropyridine-4-ylacetyl)-4-mesyloxypiperidine of the present invention is a compound represented by the formula (12):

[Chem. 20]

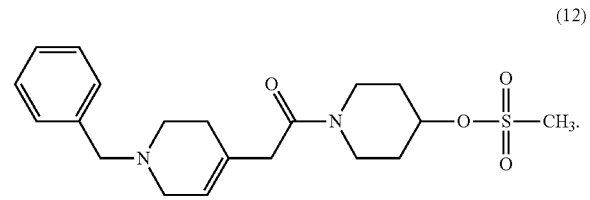 [SMILES: CS(=O)(=O)OC1CCN(C(=O)CC2=CCN(Cc3ccccc3)CC2)CC1]

(12)

1-(1-benzyl-1,2,3,6-tetrahydropyridine-4-ylacetyl)-4-mesyloxypiperidine may be prepared by using 1-(1-benzyl-1,2,3,6-tetrahydropyridine-4-ylacetyl)-4-hydroxypiperidine as the hydroxypiperidine derivative in the step (D). 1-(1-benzyl-1,2,3,6-tetrahydropyridine-4-ylacetyl)-4-mesyloxypiperidine is useful for an intermediate of a medicine.

<<Function>>

In the preparation method of the present invention, a nucleophilic reaction with an amine (4-hydroxypiperidine) could be selectively caused to the piperidylidene acetic acid derivative. The product obtained by this reaction was a mixture of isomers of hydroxypiperidine derivative. However, N-alkoxycarbonyl piperidine derivative with few impurities could be obtained by carrying out the reaction step of mesylation, and the reaction step of debenzylation, tert-butoxycarbonylation, and olefin reduction. It is surprising that a highly pure N-alkoxycarbonyl piperidine derivative wherein the amount of by-products is extremely small, can be obtained even though a mixture of isomers is used as an intermediate and multiple reactions are carried out in one step.

EXAMPLES

The present invention will now be further illustrated by, but is by no means limited to, the following Examples.

Example 1

Synthesis of 1-(1-tert-butoxycarbonyl-4-piperidylacetyl)-4-mesyloxypiperidine

[Step 1]

Synthesis of 1-benzyl-4-piperidylidene Acetic Acid Ethyl Ester

It was synthesized by the following method described in Step 1 of Example 1 of Patent literature 2.

To a mixture of ethyl diethylphosphonoacetate (235.4 g; 1.05 mol), toluene (618 g), and ethanol solution containing 20% sodium ethoxide (374.3 g; 1.10 mol in terms of sodium ethoxide), a mixed solution of 1-benzyl-4-piperidone (189.3 g; 1.00 mol) and toluene (190 g) was added dropwise at 5 to 15° C. After reacting at the same temperature for 1 hour, the reaction mixture was washed with water three times at room temperature. The organic layer was dried with anhydrous magnesium sulfate and then concentrated under reduced pressure to obtain 247.2 g of the above-referenced compound as an orange oily residue (yield 95.3%).

[Step 2]

Synthesis of a Mixture of 1-(1-benzyl-4-piperidylideneacetyl)-4-hydroxypiperidine and 1-(1-benzyl-1,2,3,6-tetrahydropyridine-4-ylacetyl)-4-hydroxypiperidine 1-benzyl-4-piperidylidene acetic acid ethyl ester (4.00 g; 0.015 mol), toluene (16.0 g), and a methanol solution containing 4-hydroxypiperidine (1.64 g; 0.016 mol) and 28% sodium methoxide (1.49 g; 0.008 mol in terms of sodium methoxide) were applied to a reaction flask (volume of 30 mL), and the mixture was heated and reacted at a reflux temperature of 108 to 112° C. for 3 hours. After completion of the reaction, the reaction mixture was cooled to room temperature. Then, brine was added thereto, and further 2.80 g of 10% hydrochloric acid was added thereto. The reactant was extracted with toluene, and the obtained organic layer was concentrated under reduced pressure. 5.36 g of the above-referenced compound was obtained as a brown oily residue.

Mass spectrometry (EI): 315 (M+H)

1-(1-benzyl-4-piperidylideneacetyl)-4-hydroxypiperidine $^1$HNMR (CDCl$_3$) δ (ppm): 1.47 (m, 2H), 1.84 (m, 2H), 2.30 (t, J=5.7 Hz, 2H), 2.49 (s, 4H), 2.50 (t, J=6.1 Hz, 2H), 2.77 (br, 1H), 3.18 (m, 2H), 3.51 (s, 2H), 3.79 (m, 1H), 3.88 (m, 1H), 4.06 (m, 1H), 5.74 (s, 1H), 7.30 (m, 5H)

1-(1-benzyl-1,2,3,6-tetrahydropyridine-4-ylacetyl)-4-hydroxypiperidine $^1$HNMR (CDCl$_3$) δ (ppm): 1.47 (m, 2H), 1.84 (m, 2H), 2.14 (s, 2H), 2.59 (t, J=5.7 Hz, 2H), 2.77 (br, 1H), 2.98 (s, 2H), 3.06 (s, 2H), 3.18 (m, 2H), 3.57 (s, 2H), 3.69 (m, 1H), 3.88 (m, 1H), 4.06 (m, 1H), 5.44 (t, J=1.6 Hz, 1H), 7.30 (m, 5H)

[Step 3]

Synthesis of 1-(1-tert-butoxycarbonyl-4-piperidylacetyl)-4-hydroxypiperidine The mixture (5.36 g; 0.017 mol) of 1-(1-benzyl-4-piperidylideneacetyl)-4-hydroxypiperidine and 1-(1-benzyl-1,2,3,6-tetrahydropyridine-4-ylacetyl)-4-hydroxypiperidine obtained in step 2, 2-propanol (44.5 g), di-tert-butyl dicarbonate (3.72 g; 0.017 mol) and 5% palladium-carbon (1.07 g) containing 50% water were applied to an autoclave (volume of 200 mL), and the mixture was reacted under a hydrogen pressure of 0.5 MPa for 6 hours at 45° C. The reaction mixture was cooled to room temperature, and the catalyst was filtered off. The filtrate was concentrated under reduced pressure to obtain 5.37 g of the above-referenced compound as an oily residue (yield: 85.9%).

[Step 4]

Synthesis of 1-(1-tert-butoxycarbonyl-4-piperidylacetyl)-4-mesyloxypiperidine 1-(1-tert-butoxycarbonyl-4-piperidylacetyl)-4-hydroxypiperidine (5.37 g; 0.016 mol) obtained in step 3, toluene (48.4 g) and triethylamine (2.16 g; 0.021 mol) were applied to a reaction flask (volume of 100 mL). Mesyl chloride (1.88 g; 0.016 mol) was added thereto dropwise at 0 to 10° C., and the mixture was reacted at the same temperature for 1 hour. The reactant was washed with aqueous solution of sodium hydrogen carbonate and brine, and concentrated under reduced pressure to obtain 6.11 g of the above-referenced compound as the brown oily residue (yield; 93.3%). Toluene (21.5 g) was added to the concentrated residue and the mixture was ice-cooled, and the precipitated crystal was collected by filtration. The wet crystal was dried under reduced pressure to obtain the above-referenced compound as a slightly yellow crystalline powder. The results of analysis of $^1$HNMR and $^{13}$CNMR of the obtained compound were similar to the results described in Example 2 of Patent literature 2.

Example 2

Synthesis of 1-(1-tert-butoxycarbonyl-4-piperidylacetyl)-4-mesyloxypiperidine

[Step 1]

Synthesis of a Mixture of 1-(1-benzyl-4-piperidylideneacetyl)-4-mesyloxypiperidine and 1-(1-benzyl-1,2,3,6-tetrahydropyridine-4-ylacetyl)-4-mesyloxypiperidine The mixture (12.0 g; 38 mmol) of 1-(1-benzyl-4-piperidylideneacetyl)-4-hydroxypiperidine and 1-(1-benzyl-1,2,3,6-tetrahydropyridine-4-ylacetyl)-4-hydroxypiperidine obtained by the step 2 of Example 1, triethylamine (4.52 g; 0.045 mol), and toluene (108.0 g) were applied to a four-necked flask (volume of 300 mL), and the mixture was cooled to 4° C. Mesyl chloride (4.72 g; 0.041 mol) was added thereto dropwise at 0 to 10° C., and the mixture was reacted at the same temperature for 1 hour. The reactant was washed with aqueous solution of sodium hydrogen carbonate and brine, and concentrated under reduced pressure to obtain 12.4 g of the above-referenced compound as the oily residue (yield; 83.0%).

Mass spectrometry (EI): 393 (M+H)

1-(1-benzyl-4-piperidylideneacetyl)-4-mesyloxypiperidine $^1$HNMR (CDCl$_3$) δ (ppm): 1.84 (m, 2H), 1.96 (m, 2H), 2.31 (t, J=5.7 Hz, 2H), 2.41 (s, 1H), 2.50 (m, 1H), 2.51 (d, J=4.7 Hz, 4H), 3.04 (s, 3H), 3.46 (m, 1H), 3.52 (s, 2H), 3.54 (m, 1H), 3.73 (m, 1H), 3.82 (m, 1H), 4.92 (m, 1H), 5.74 (s, 1H), 7.25 (m, 5H)

1-(1-benzyl-1,2,3,6-tetrahydropyridine-4-ylacetyl)-4-mesyloxypiperidine $^1$HNMR (CDCl$_3$) δ (ppm): 1.84 (m, 2H), 1.96 (m, 2H), 2.14 (s, 2H), 2.59 (t, J=8.0 Hz, 2H), 2.98 (s, 2H), 3.04 (s, 3H), 3.07 (s, 2H), 3.37 (m, 1H), 3.54 (m, 1H), 3.58 (s, 2H), 3.64 (m, 1H), 3.82 (m, 1H), 4.92 (m, 1H), 5.45 (s, 1H), 7.25 (m, 5H)

[Step 2]

Synthesis of 1-(1-tert-butoxycarbonyl-4-piperidylacetyl)-4-mesyloxypiperidine The mixture (1.60 g; 0.004 mol) of 1-(1-benzyl-4-piperidylideneacetyl)-4-mesyloxypiperidine and 1-(1-benzyl-1,2,3,6-tetrahydropyridine-4-ylacetyl)-4-mesyloxypiperidine obtained in step 1, di-tert-butyl dicarbonate (0.89 g; 0.004 mol), 2-propanol (13 g), and 5% palladium-carbon (0.96 g) containing 50% water were applied to an autoclave (volume of 200 mL), and the mixture was reacted under a hydrogen pressure of 0.5 MPa for 10 hours at 50° C. The reaction mixture was cooled to room temperature, and the catalyst was filtered off. The filtrate was concentrated under reduced pressure. The concentrated residue was washed with toluene and brine, and concentrated under reduced pressure to obtain 1.36 g of the above-referenced compound as the colorless oil (yield; 82.5%). Toluene (1.65 g) was added to the concentrated residue, and ice-cooled, and the precipitated crystal was collected by filtration. The wet crystal was dried under reduced pressure to obtain 0.70 g of the above-referenced compound as a white crystalline powder (yield; 42.5%). The results of analysis of $^1$HNMR and $^{13}$CNMR of the obtained compound were similar to the results described in Example 2 of Patent literature 2

INDUSTRIAL APPLICABILITY

The N-alkoxycarbonyl piperidine derivative, such as 1-(1-tert-butoxycarbonyl-4-piperidylacetyl)-4-mesyloxypiperidine, obtained by the preparation method of the present invention is useful for an intermediate for synthesizing medicine.

The invention claimed is:

1. A method for preparing a hydroxypiperidine derivative, comprising a step of:

(A) reacting a piperidylidene acetic acid derivative represented by the formula (1):

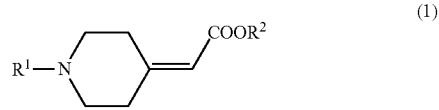

(1)

wherein R¹ is an arylmethyl group which may have a substituent group, and R² is an alkyl group, with 4-hydroxypiperidine in the presence of base, to obtain a hydroxypiperidine derivative represented by the formula (2) or the formula (3):

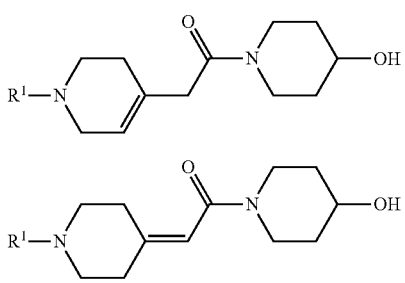

wherein R¹ is an arylmethyl group which may have a substituent group.

2. A method for preparing an N-alkoxycarbonyl piperidine derivative, comprising the steps of:
(A) according to claim 1,
(B) reacting the hydroxypiperidine derivative obtained in the step (A) with a dicarbonate represented by the formula (4):

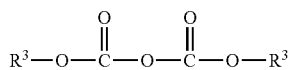

wherein R³ is alkyl group, in the presence of hydrogen and a catalyst containing palladium,
to obtain an alkoxycarbonyl derivative represented by the formula (5):

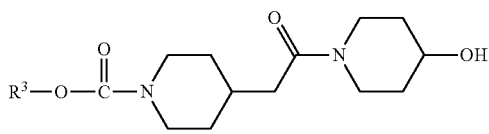

wherein R³ is an alkyl group, and
(C) reacting the alkoxycarbonyl derivative with mesyl halide in the presence of base, to obtain an N-alkoxycarbonyl piperidine derivative represented by the formula (6):

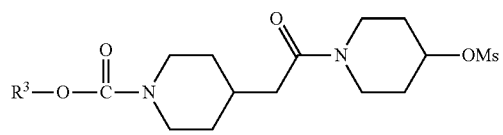

wherein R³ is an alkyl group, and Ms is a mesyl group.

3. A method for preparing an N-alkoxycarbonyl piperidine derivative, comprising the steps of:
(A) according to claim 1,
(D) reacting the hydroxypiperidine derivative obtained in the step (A) with mesyl halide in the presence of base, to obtain a mesyloxypiperidine derivative represented by the formula (7) or the formula (8):

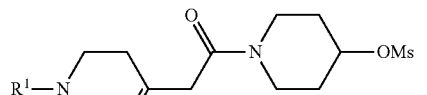

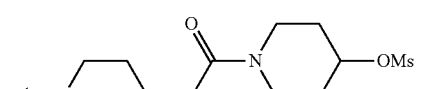

wherein R¹ is an arylmethyl group which may have a substituent group, and
(E) reacting the mesyloxypiperidine derivative with a dicarbonate represented by the formula (4):

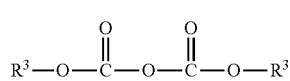

wherein R³ is alkyl group, in the presence of hydrogen and a catalyst containing palladium, to obtain an N-alkoxycarbonyl piperidine derivative represented by the formula (6):

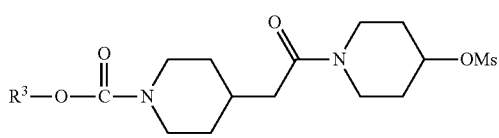

wherein R³ is an alkyl group, and Ms is a mesyl group.

4. 1-(1-benzyl-4-piperidylideneacetyl)-4-hydroxypiperidine represented by the formula (9):

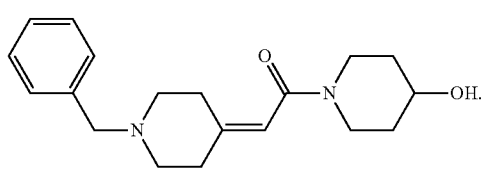

5. 1-(1-benzyl-1, 2, 3, 6-tetrahydropyridine-4-ylacetyl)-4-hydroxypiperidine represented by the formula (10):

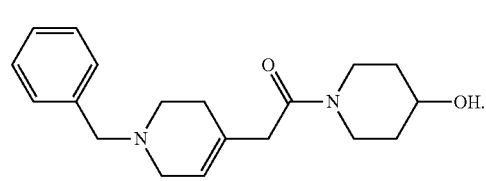

6. 1-(1-benzyl-4-piperidylideneacetyl)-4-mesyloxypiperidine represented by the formula (11):

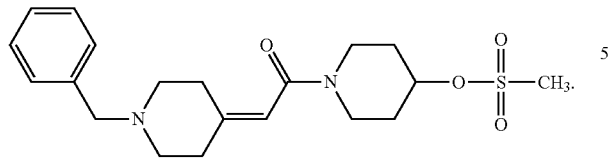
(11)
7. 1-(1-benzyl-1, 2, 3, 6-tetrahydropyridine-4-ylacetyl)-4-mesyloxypiperidine represented by the formula (12):
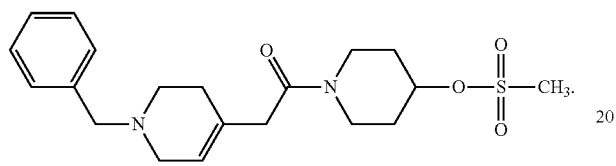
(12)
* * * * *